United States Patent [19]
Perry

[11] Patent Number: 6,153,578
[45] Date of Patent: Nov. 28, 2000

[54] FRAGRANCE RELEASING OLEFINIC SILANES

[75] Inventor: Robert J. Perry, Niskayuna, N.Y.

[73] Assignee: General Electric Company, Pittsfield, Mass.

[21] Appl. No.: 09/385,319

[22] Filed: Aug. 30, 1999

Related U.S. Application Data

[62] Division of application No. 09/143,136, Aug. 28, 1998, Pat. No. 6,046,156.

[51] Int. Cl.$^7$ ................................. A61K 7/46; C07F 7/04
[52] U.S. Cl. ................................. 512/27; 512/2; 512/25; 512/26; 556/466; 556/482; 556/484; 556/485
[58] Field of Search ........................ 512/2, 25, 26, 512/27; 556/466, 482, 484, 485

[56] References Cited

U.S. PATENT DOCUMENTS

| | | |
|---|---|---|
| 2,679,496 | 5/1954 | Bunnell . |
| 3,215,719 | 11/1965 | Allen et al. . |
| 3,271,305 | 9/1966 | Allen et al. . |
| 3,779,987 | 12/1973 | Bazzano . |
| 4,083,861 | 4/1978 | Seiler et al. ........................ 556/413 |
| 4,445,641 | 5/1984 | Baker et al. . |
| 4,500,725 | 2/1985 | Yemoto et al. . |
| 4,524,018 | 6/1985 | Yemoto et al. . |
| 4,908,208 | 3/1990 | Lee et al. . |
| 5,008,115 | 4/1991 | Lee et al. . |
| 5,071,704 | 12/1991 | Fischel-Ghodsian . |
| 5,130,171 | 7/1992 | Prud'Homme et al. . |
| 5,160,494 | 11/1992 | Krzysik et al. . |
| 5,176,903 | 1/1993 | Goldberg et al. . |
| 5,185,155 | 2/1993 | Behan et al. . |
| 5,234,689 | 8/1993 | Lindauer et al. . |
| 5,324,444 | 6/1994 | Berry et al. . |
| 5,372,806 | 12/1994 | Holloway . |
| 5,387,411 | 2/1995 | Abrutyn et al. . |
| 5,387,622 | 2/1995 | Yamamoto . |
| 5,449,512 | 9/1995 | Simmons . |
| 5,490,982 | 2/1996 | Siciliano . |
| 5,500,223 | 3/1996 | Behan et al. . |
| 5,508,259 | 4/1996 | Holzner et al. . |
| 5,525,555 | 6/1996 | Zank . |
| 5,525,588 | 6/1996 | Michetti . |

FOREIGN PATENT DOCUMENTS

| | | |
|---|---|---|
| 0878497A2 | 11/1998 | European Pat. Off. . |
| 07179328A | 7/1995 | Japan . |
| 2041964 | 9/1980 | United Kingdom . |
| WO 9628497 | 9/1996 | WIPO . |
| Wo 96/28497 | 9/1996 | WIPO . |

*Primary Examiner*—Maureen M. Wallenhorst
*Assistant Examiner*—Monique T. Cole

[57] ABSTRACT

Fragrant silanes having the formula:

$$(R^1O)_a(R^2O)_b(R^3O)_c(R^4)_d(R^5)_e SiR^6$$

where $R^1$, $R^2$ and $R^3$ are derived from the group of alcohols consisting of $R^1OH$, $R^2OH$ and $R^3OH$ wherein $R^1OH$, $R^2OH$ and $R^3OH$ are fragrant alcohols or alternatively $R^1$, $R^2$ and $R^3$ are derived from the group of fragrant esters, ketones, or aldehydes having the structure:

$$R^7-CH_2(C=O)-R^8$$

wherein the fragrant ester, ketone or aldehyde is capable of exhibiting the enol form of the carbonyl moiety under reaction conditions, with $R^4$ and $R^5$ selected from the group consisting of monovalent hydrocarbon radical having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms.

7 Claims, No Drawings

FRAGRANCE RELEASING OLEFINIC SILANES

CROSS-REFERENCE TO RELATED APPLICATIONS

This is a divisional of application Ser. No. 09/143,136 filed on Aug. 28, 1998 now U.S. Pat. No. 6,046,156 Apr. 4, 2000.

STATEMENT REGARDING FEDERALLY FUNDED RESEARCH

Not Applicable

FIELD OF THE INVENTION

The present invention relates to silanes that contain a terminal olefinic moiety and one or more substituent groups derived from fragrant compounds wherein the fragrant compound is regenerated and released by a hydrolysis reaction.

BACKGROUND OF THE INVENTION

The slow sustained release of a fragrant molecule is a highly desirable trait in many personal care products. A number of means have been proposed and implemented to achieve this goal. Among these means are dissolving or suspending fragrant compounds in personal care emulsions (U.S. Pat. Nos. 5,525,588; 5,525,555; 5,490,982; and 5,372,806), encapsulation of a fragrant compound (U.S. Pat. Nos. 5,500,223; 5,324,444; 5,185,155; 5,176,903; and 5,130,171), dissolving a fragrant compound into a hydrophobic phase such as a silicone (U.S. Pat. Nos. 5,449,512; 5,160,494 and 5,234,689), incorporation of a fragrant compound into cross-linked polymers (U.S. Pat. Nos. 5,387,622 and 5,387,411), incorporation of fragrant compounds into permeable laminates (U.S. Pat. Nos. 5,071,704 and 5,008,115), incorporation of fragrant compounds into matrices that soften at body temperature (U.S. Pat. No. 4,908,208), incorporation of fragrant compounds into rate controlling membranes (U.S. Pat. No. 4,445,641) and derivatization of silanes with fragrant alcohols to form alkoxy silanes (U.S. Pat. Nos. 4,524,018 and 4,500,725). None of these approaches teach or suggest that an olefinically substituted silane containing one or more fragrant substituent groups can be prepared or if prepared would be useful in the preparation of personal care compositions.

SUMMARY OF THE INVENTION

The present invention provides for the reaction product of a fragrant alcohol and an olefinic halosilane or an olefinic silicon alkoxide. The present invention also provides for a silicon compound having the formula:

$$(R^1O)_a(R^2O)_b(R^3O)_c(R^4)_d(R^5)_e SiR^6$$

where $R^1$, $R^2$ and $R^3$ are derived from the group of fragrant alcohols consisting of $R^1OH$, $R^2OH$ and $R^3OH$ with $R^4$ and $R^5$ selected from the group consisting of monovalent hydrocarbon radical having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3.

The present invention further provides for the reaction product of a fragrant aldehyde, ketone or ester and an olefinic halosilane or an olefinic silicon alkoxide; and also a silicon compound having the formula:

$$(R^1)_a(R^2)_b(R^3)_c(R^4)_d(R^5)_e SiR^6$$

where $R^1$, $R^2$ and $R^3$ each independently have the structure:

$$R^7-CH=C(O-)-R^8$$

wherein $R^7$ and $R^8$ are independently chosen for each $R^1$, $R^2$ and $R^3$, with $R^4$ and $R^5$ selected from the group consisting of monovalent hydrocarbon radicals having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms.

DETAILED DESCRIPTION OF THE INVENTION

The compounds of the present invention introduce fragrant moieties into an olefinic silane molecule. The olefinic silane molecule is capable of further reaction under hydrosilylation conditions to form a variety of siloxanes that also possess fragrant moieties. These siloxane molecules are useful in a variety of personal care compositions. The present invention is directed to new compositions of matter that are silanes that release a fragrant alcohol, ester, ketone or aldehyde upon particular subsequent chemical reactions. Typically the subsequent chemical reaction that releases the fragrant alcohol is a hydrolysis reaction. Furthermore these silanes may be reacted to form siloxanes that release a fragrant alcohol upon the same particular subsequent chemical reactions wherein the olefinic silane precursor also releases a fragrant alcohol, ester, ketone or aldehyde.

The compounds of the present invention are described by the formula:

$$(R^1O)_a(R^2O)_b(R^3O)_c(R^4)_d(R^5)_e SiR^6$$

where $R^1$, $R^2$ and $R^3$ are selected (or derived from) from the group of alcohols consisting of $R^1OH$, $R^2OH$ and $R^3OH$ wherein $R^1OH$, $R^2OH$ and $R^3OH$ are fragrant alcohols or alternatively are derived from the group of fragrant esters, ketones, or aldehydes having the structure:

$$R^7-CH_2(C=O)-R^8$$

wherein the fragrant ester, ketone or aldehyde is capable of exhibiting the enol form of the carbonyl moiety under reaction conditions as shown:

$$R^7-CH_2(C=O)-R^8 \rightarrow R^7-CH=C(OH)-R^8$$

and which will react through the enol hydroxyl group to form a carbon-oxygen-silicon linkage, for example $R^7-CH=C(O-)-R^8$ where the hyphen after the oxygen in the formula indicates the species is a monovalent radical, with $R^4$ and $R^5$ selected from the group consisting of monovalent hydrocarbon radical having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms. It should be noted that the structure:

$$R^7—CH=C(O—)—R^8$$

is a conjugate structure that corresponds to the enolate structure:

$$R^7—CH=C(OH)—R^8$$

but missing the hydroxyl hydrogen. In the structure:

$$R^7—CH=C(O—)—R^8$$

the hyphen after the oxygen atom indicates a univalent bonding site wherein the structure is a monovalent radical and through which the radical is bonded as a substituent. Thus when the fragrant moiety is derived from an aldehyde, ketone or ester the fragrant silicon compound has the formula:

$$(R^1)_a(R^2)_b(R^3)_c(R^4)_d(R^5)_e SiR^6$$

where $R^1$, $R^2$ and $R^3$ each independently have the structure:

$$R^7—CH=C(O—)—R^8$$

with all the variables as previously defined. As used herein the phrase from one to one hundred carbon atoms is chosen wherein the class of available fragrant esters, ketones, and aldehydes is subtended by the formula $R^7—CH_2(C=O)—R^8$. As used herein, the phrase monovalent hydrocarbon radical includes both aliphatic and aromatic monovalent hydrocarbon radicals that may also include hetero-atoms such as oxygen, nitrogen, sulfur and the halogens, fluorine, chlorine, bromine and iodine.

The following synthetic examples are intended to illustrate the general synthetic reactions schemes that a person having ordinary skill in the art of silicones chemistry would typically employ in order to prepare the compounds of the present invention. These reaction schemes are thus illustrative only and do not represent the only synthetic pathways by which the compounds of the present invention may be prepared.

When the starting material is a fragrant alcohol such as phenethanol, olefinic halosilanes or olefinic silicon alkoxides may be employed as starting materials to produce the fragrance-releasing silanes of the present invention. Applicant herewith defines the phrase olefinic silicon alkoxide to be a monomeric silicon compound wherein a single silicon atom is substituted with four monovalent organic substituents one of which is an olefin and one of which is an alkoxide.

Reaction scheme I

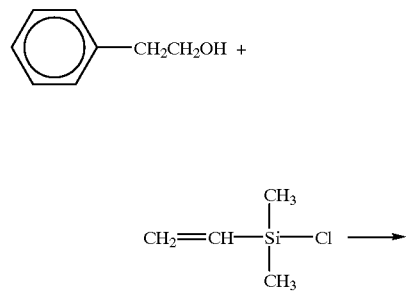

Reaction scheme II

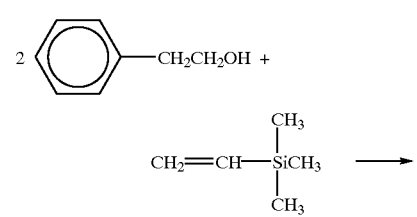

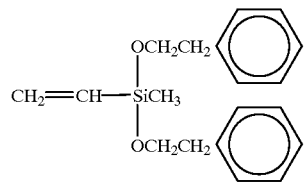

Reaction scheme III

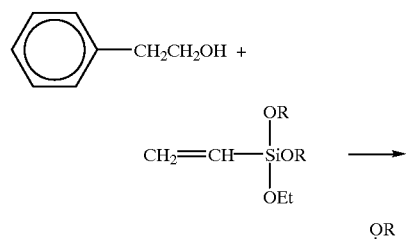

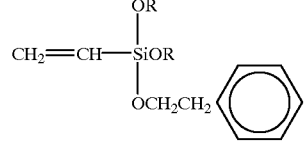

Where the R groups for reaction III may be Et ($C_2H_5$-) or —$CH_2CH_2C_6H_5$. Similarly 3-methyl-5-(2,2,3,-trimethyl-3-cyclopenten-1-yl)-4-penten-2-ol will react with chloromethylvinylsilane in a similar fashion, reaction scheme IV:

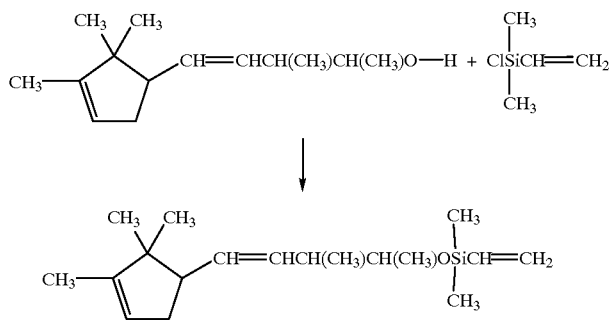

as will allyldimethylchlorosilane react with citronellol in a similar, reaction scheme V:

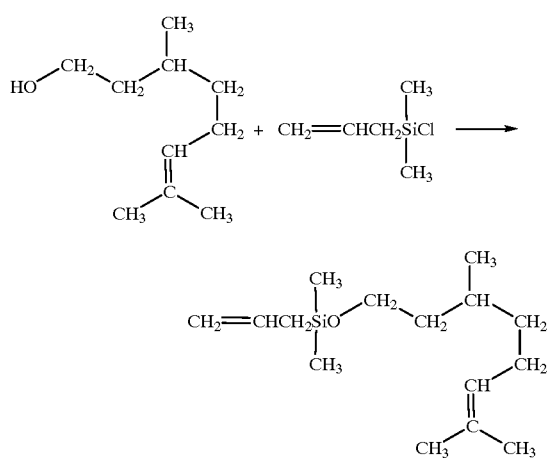

An example of the reaction scheme using a fragrant carbonyl containing moiety, 2-methyl-3-(4-t-butylphenyl)propanal, reaction VI:

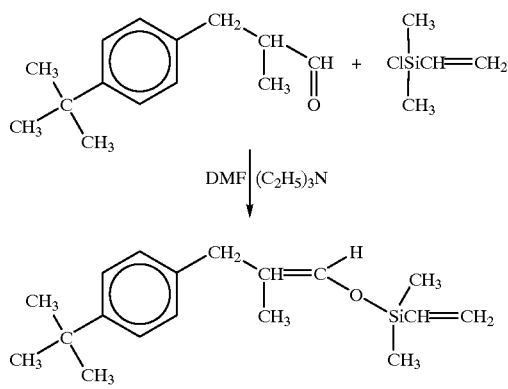

Note that DMF is dimethylformamide. Reaction scheme VI may also be used to prepare the 3-methyl-3-(3-(1-methylethylphenyl))propanal derivative:

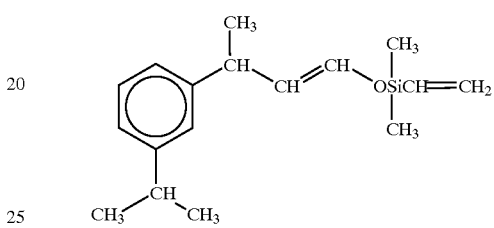

The reaction of fragrant carbonyl containing species, i.e. esters, ketones and aldehydes, requires the establishment of the keto enol tautomeric equilibrium previously referred to which is assisted by a base such as triethylamine.

Tautomerism is the chemical phenomenon of the establishment of an equilibrium between two or more structurally distinct compounds. In nearly all cases, the difference between one tautomeric form of the equilibrium compounds and the other is the isomeric placement of a hydrogen atom. A prevalent form of tautomerism is the tautomeric equilibrium established between a carbonyl compound (for example one containing a carbonyl group) and having a hydrogen atom alpha to the carbonyl group, for example an α hydrogen:

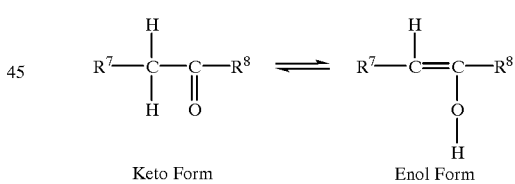

Keto Form          Enol Form

Generally the equilibrium constant favors the keto form and the equilibrium lies well to the left. The extent of enolization is greatly affected by solvent, concentration and temperature. When a strong base is present, both the enol and the keto form can lose a hydrogen ion (a proton), forming an enolate anion:

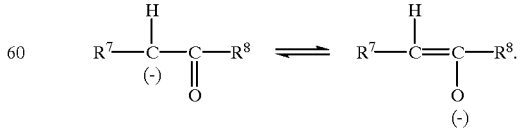

Since both of these structures differ only in the placement of electrons, these are canonical forms of the same ion rather than tautomeric isomers. Because oxygen is more electronegative than carbon, the predominate canonical form is the one where the ionic charge is more localized on the oxygen atom. While the tautomeric equilibrium between enols and ketones or aldehydes is not normally a preparative reaction, the equilibrium must occur since ketones and aldehydes often react through their enol forms as they do instantly in the preparation of the compounds of the present invention. For a more detailed explanation of this chemistry see J. March "Advanced Organic Chemistry," John Wiley & Sons, New York (1985), pp. 66–68 and 527–529 and references therein.

The fragrant alcohols that are precursors of the silanes of the present invention are selected from the group consisting of 3-methyl-5-(2,2,3,-trimethyl-3-cyclopenten-1-yl)4-penten-2-ol, 2-methylbutanol, 3-pentanol, n-pentanol, 2-pentanol, n-hexanol, 2-methylpentanol, 1-decanol, sandela, nonadyl, dimetol, thymol, 1-heptanol, menthol, eugenol, vanillan, o-vanillan, 4-(p-hydroxyphenyl)-2-butanone, syringealdehyde, prenol, cis-3-hexanol, trans-3-hexanol, cis-4-heptenol, trans-2-octenol, trans-2-cis-6-nonadienol, geraniol, nerol, citronellol, crotyl alcohol, oleyl alcohol, linalool, α-terpineol, β-phenethyl alcohol, cinnamic alcohol, benzyl alcohol, α-methylbenzyl alcohol, nonyl alcohol, 1-octanol, 3-octanol, phenethyl salicylate, hydrocinnayl alcohol, cis-6-nonen-1-ol, trans-2-nonen-1-ol, methyl salicylate, cis-3-octen-ol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool and 2-phenoxyethanol.

The fragrant carbonyl containing species are selected from the group consisting of 3-methyl-3-(3-(1-methylethylphenyl))propanal, 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamen aldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate.

The fragrance releasing compounds of the present invention are particularly suited to incorporation into personal care products to impart a desirable long lasting fragrance to the products. Suitable uses include but are not limited to deodorants, antiperspirants, skin creams, facial creams, hair care products such as shampoos, mousses, styling gels, protective creams, shaving creams, after shave, cologne, perfume, color cosmetics such as lipsticks, foundations, blushes, makeup, and mascara; and other cosmetic formulations where other silicon containing components have been added and where it is desirable to impart a fragrance. Incorporation of small amounts of the compositions of the present invention into fragrance products such as shaving lotions, colognes, toilet water, and perfumes can impart a desirable long lasting fragrance to these products. Further, the silanes of the present invention may incorporated into other products where it is desirable to mask unpleasant odors with a pleasant fragrance for example household cleaning products such as waxes and polishes, automobile cleaning products such as waxes and polishes, detergents, textile coatings, paints, varnishes and the like subject to the limitation that the silane of the present invention be compatible or capable of being rendered compatible with the product in which it is incorporated.

Experimental

Preparation of Dimethylvinylphenethyloxysilane,—Dimethylvinylchlorosilane (150 mL, 1.099 moles) was added to a stirred solution of phenethyl alcohol (124.5 mL, 1.042 moles), triethylamine (TEA, 155 mL, 1.112 moles) and toluene (300 mL) over 1.5 h. After addition, the reaction was heated to 65° C. for 0.5 h then cooled to room temperature, filtered, the filter cake washed with toluene (200 mL), the filtrate concentrated in vacuo and then vacuum distilled (81–85° C./4 mm Hg) to give product (180.5 g, 84%).

Bis(phenethyloxy)methylvinylsilane,—Dichloromethylvinylsilane (80 g, 0.567 moles) was added to a stirred solution of phenethyl alcohol (140 g, 114 moles), triethylamine (TEA, 121 g, 1.2 moles) and Isopar C (700 mL) over one hour during which time the reaction mixture was heated to 70° C. After an additional one hour, the reaction was cooled to room temperature, filtered, concentrated in vacuo and then stripped under high vacuum distilled (110° C. at 4 mm Hg) to give product (166 g, 94%).

Phenethyloxydiethoxymethylvinylsilane,—Triethoxyvinylsilane (200 g, 1.05 moles), phenethyl alcohol (128 g, 1.05 moles) and Filtrol-20(5 g) were added together and heated to 90° C. Ethanol (EtOH) was distilled off as it formed and the reaction was stopped when most of the phenethyl alcohol had been consumed. The reaction mixture was then stripped at 90° C./4 mm Hg to give a mixture of products which had the following distribution: 45% product in which both OR=OEt, 39% product in which one OR=OEt and one OR=phenethyloxy, and 8% product in which both OR =phenethyloxy.

Dimethyl(3-methyl-5-(2,2,3,-trimethyl-3-cyclopenten-1-yl)-4-penten-2-oxy)vinylsilane,—Dimethylchlorovinylsilane (10.0 mL, 0.073 moles) diluted with toluene (25 mL), was added to a stirred solution of 3-methyl-5-(2,2,3,-trimethyl-3-cyclopenten-1-yl)4-penten-2-ol (16.40 g, 0.077 moles), triethylamine (TEA, 7.8 g, 0.077 moles) and toluene (100 mL) over 20 min during. The mixture was then heated to 60° C. After 6 hours, the reaction was cooled to room temperature, filtered, concentrated in vacuo and then stripped and distilled under high vacuum distilled (75–77° C./0.3 mm Hg) to give product (166 g, 94%).

Dimethylvinyl(2-methyl-3-(4-t-butylphenyl)propenoxy) silane—A 100 mL 3-neck round bottom flask equipped with a stir-bar, a thermometer, a condenser and a nitrogen inlet was charged with dimethylvinylchlorosilane (4.1 mL, 0.030 moles), 2-methyl-3-(4-t-butylphenyl)propanal, (5.0 g, 0.024 moles), triethylamine and N,N-dimethylformamide (DMF, 20 mL) and heated to 80° C. for 22 h. the mixture was diluted with 100 mL of Isopar-C, and the mixture was washed three times with cold saturated aqueous sodium bicarbonate, then cold 1N HCl, then bicarbonate, then dried over $MgSO_4$ and stripped to give 6.4 g (90%) product.

Dimethyl(3-methyl-3-(1-methylethylphenyl)propenoxy) vinylsilane—A 500 mL 3-neck round bottom flask equipped with a stir-bar, a thermometer, a condenser and a nitrogen inlet was charged with dimethylvinylchlorosilane (44 mL, 0.322 moles), 3-methyl-3-(3-(1-methylethylphenyl))

propanal (50 g, 0.263 moles), triethylamine (90 mL, 0.644 moles) and N,N-dimethylformamide (DMF, 200 mL) and heated to 80° C. for 22 h. The mixture was diluted with 200 mL of Isopar-C, and the mixture was washed three times with cold saturated aqueous sodium bicarbonate, then cold 1N HCl, then bicarbonate, then dried over $MgSO_4$ and stripped and distilled (85–95° C./0.07 mm Hg) to give 40.7 g (61%) product.

Dimethyl(4-methyl-2-penten-2-oxy)vinylsilane—A 500 mL 3-neck round bottom flask equipped with a stir-bar, a thermometer, a condenser and a nitrogen inlet was charged with dimethylvinylchlorosilane (14.5 g, 0.12 moles), 4-methyl-2-pentanone (10 g, 0.10 moles), triethylamine (24.3 g, 0.24 moles) and N,N-dimethylformamide (DMF, 75 mL) and heated to 80° C. for 40 h. The mixture was filtered to remove solid, diluted with 100 mL water, then extracted with hexanes (3×100 mL). The extracts were combined, washed with water (2×50 mL), then dried over $MgSO_4$ and stripped and distilled (160–162° C.) to give 10.1 g (55%) product.

What is claimed is:

1. A silicon compound having the formula:

$$(R^1)_a(R^2)_b(R^3)_c(R^4)_d(R^5)_e SiR^6$$

where $R^1$, $R^2$ and $R^3$ and are derived from the group of fragrant aldehyde, ketone or ester consisting of 3-methyl-3 (3-(1-methylethylphenyl))propanal), 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamenaldehyde, 4-(p-methoxyphenyl)-2butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate; and $R^5$ selected from the group consisting of monovalent hydrocarbon radicals having from one to forty carbon atoms and monovalent alkoxy radicals having from one to forty carbon atoms, $R^6$ a two to forty atom monovalent unsaturated hydrocarbon radical containing a terminal olefinic or acetylenic moiety, where the subscript a has a value ranging from 1 to 3 and the subscripts b, c, d, and e have values ranging from 0 to 2 subject to the limitation that a+b+c+d+e=3.

2. The silicon compound of claim 1, wherein the subscript a has a value of 2.

3. The silicon compound of claim 1, wherein the subscript a has a value of 3.

4. A composition comprising a silicon compound having the formula:

$$(R^1)_a(R^2)_b(R^3)_c(R^4)_d(R^5)_e SiR^6$$

where $R^1$, $R^2$ and $R^3$ and are derived from the group of fragrant aldehyde, ketone or ester consisting of 3-methyl-3 (3-(1-methylethylphenyl))propanal), 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamenaldehyde, 4-(p-methoxyphenyl)-2butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate; with $R^4$ and $R^5$ selected from the group consisting of monovalent hydrocarbon radicals having from one to forty carbon atoms and monovalent alkoxy radicals having from one to forty carbon atoms, $R^6$ a two to forty atom monovalent hydrocarbon radical containing a terminal olefinic or acetylenic moiety, where the subscript a has a value ranging from 1 to 3 and the subscripts b, c, d, and e have values ranging from 0 to 2 subject to the limitation that a+b+c+d+e=3.

5. The composition of claim 4 wherein the subscript a has a value of 2.

6. The composition of claim 4 wherein the subscript a has a value of 3.

7. A cosmetic composition comprising the composition of claim 4.

* * * * *